United States Patent

Crico

[11] 4,162,201
[45] Jul. 24, 1979

[54] PURIFICATION AND RECOVERY OF ETHYLENE DICHLORIDE

[75] Inventor: Aurelio M. Crico, Corpus Christi, Tex.

[73] Assignee: PPG Industries, Inc., Pittsburgh, Pa.

[21] Appl. No.: 923,856

[22] Filed: Jul. 12, 1978

[51] Int. Cl.² .......................... B01D 3/36; C07C 19/02
[52] U.S. Cl. ........................ 203/67; 203/98; 260/652 P
[58] Field of Search ............... 203/67, 98; 260/652 P

[56] References Cited

U.S. PATENT DOCUMENTS

| | | | |
|---|---|---|---|
| 2,433,306 | 12/1947 | Teter et al. | 203/67 |
| 2,649,406 | 8/1953 | Harrison et al. | 203/67 |
| 3,076,043 | 1/1963 | Dehn | 260/652 P |
| 3,378,597 | 4/1968 | Dehn et al. | 260/652 P |

OTHER PUBLICATIONS

Azeotropic Data III, Horsley 1973, pp. 50 and 61.

Primary Examiner—Wilbur L. Bascomb, Jr.
Attorney, Agent, or Firm—Edward J. Whitfield

[57] ABSTRACT

Carbon tetrachloride and chloroform are separated as a light fraction from ethylene dichloride by distilling the ethylene dichloride under reflux conditions to maintain a chloroform concentration greater than 51.5 mole percent in the reflux liquid.

3 Claims, 2 Drawing Figures

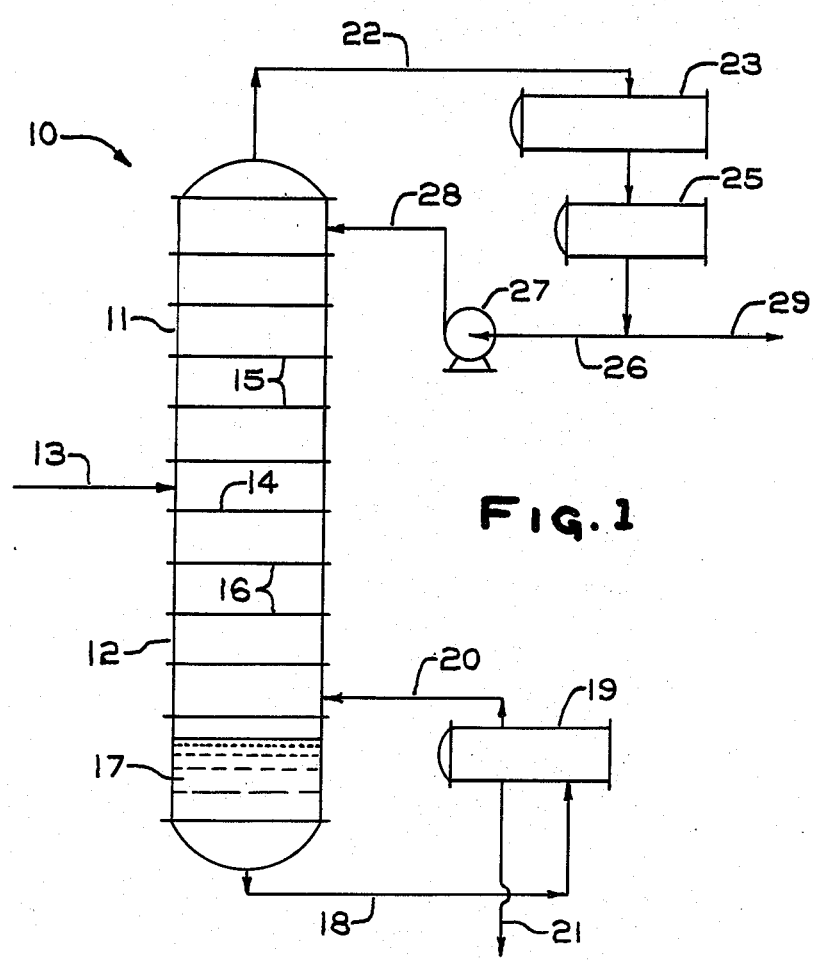
Fig. 1
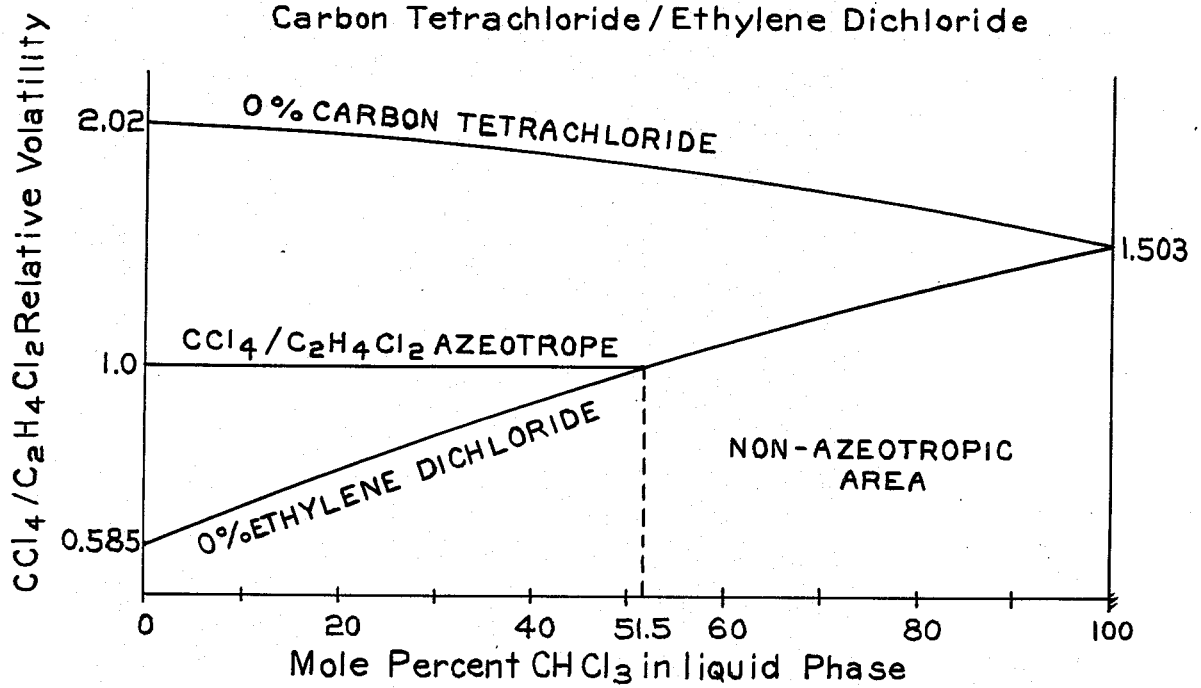
Fig. 2 Effect of Chloroform Concentration on the Relative Volatility of Carbon Tetrachloride/Ethylene Dichloride

PURIFICATION AND RECOVERY OF ETHYLENE DICHLORIDE

BACKGROUND OF THE INVENTION

Ethylene dichloride (1,2-dichloroethane) is an important starting material in the production of chlorinated hydrocarbons such as vinyl chloride, vinylidene chloride, methylchloroform, trichloroethylene, and perchloroethylene.

Ethylene dichloride is typically produced by reacting ethylene and chlorine in a liquid reaction medium or by an oxyhydrochlorination process wherein a gaseous mixture of ethylene, hydrogen chloride, and oxygen is contacted with a Deacon-type catalyst at a moderately elevated temperature.

The crude product obtained by the oxyhydrochlorination process typically assays about 97 percent ethylene dichloride and contains a number of impurities chief among which are chloroform, carbon tetrachloride, trichloroethylene, and 1,1,2-trichloroethane.

Since the purity and quality of chlorinated hydrocarbon products produced from ethylene dichloride depend on the purity of the latter, the crude ethylene dichloride must be further processed to remove or reduce the level of impurities.

Ethylene dichloride is typically purified by distillation; however, distillation is complicated by the fact that carbon tetrachloride forms an azeotrope with ethylene dichloride. Since carbon tetrachloride and chloroform are removed as light fractions upon distillation of ethylene dichloride, considerable amounts of ethylene dichloride are lost in the light fraction or distillate due to azeotropic entrainment with carbon tetrachloride. For example, a typical light distillate has been found to contain from 40 to 50 weight percent and as much as 90 weight percent ethylene dichloride.

It is desirable, therefore, to devise means of breaking the ethylene dichloride-carbon tetrachloride azeotrope to minimize loss of ethylene dichloride in the light distillate while still enabling substantially complete removal of chloroform and carbon tetrachloride impurities.

STATEMENT OF THE INVENTION

In the purification of ethylene dichloride by distillation wherein carbon tetrachloride and chloroform are separated as a light fraction, the ethylene dichloride-carbon tetrachloride azeotrope is broken by continuously refluxing the light fraction and maintaining a chloroform concentration in the reflux liquid of greater than 51.5 mole percent.

DESCRIPTION OF THE DRAWINGS

FIG. 1 is a simplified schematic drawing of a typical continuous rectifying/stripping apparatus which may be used in the practice of the process of the invention.

FIG. 2 is a diagram showing the effect of chloroform concentration on the relative volatility of an ethylene dichloride-carbon tetrachloride azeotrope in the liquid phase at atmospheric pressure.

DESCRIPTION OF THE INVENTION

In accordance with this invention, it has been found that in the purification of crude ethylene dichloride by fractional distillation, carbon tetrachloride and chloroform are separated as a light fraction by distilling the crude ethylene dichloride under reflux conditions wherein the chloroform concentration of the reflux liquid is permitted to build up to and is maintained at a concentration greater than 51.5 mole percent thereby breaking the carbon tetrachloride-ethylene dichloride azeotrope and permitting recovery of ethylene dichloride that would otherwise be lost through azeotropic entrainment in the light fraction.

With reference to FIG. 1, 10 represents a conventional continuous fractionating column having an upper rectification section 11 provided with a plurality of rectifier plates 15 and a lower stripper section 12 provided with a plurality of stripper plates 16. A liquid feed of crude ethylene dichloride is introduced via line 13 to a feed plate 14 located proximate the middle of the column 10. The liquid feed flows downwardly through the stripper section 12 and collects in a pool 17 at the bottom. The liquid is conveyed via line 18 to a reboiler 19 wherein the lower boiling components are vaporized and the vapor is returned via line 20 to the bottom of the column. Heat is supplied to the reboiler by any suitable means (not shown) such as steam, an electrical resistance heater, or a gas heater. The column is typically operated at a top pressure of from atmospheric to about 10 psig and a top temperature of from about 55° C. to about 75° C.

The vapor, containing chloroform, carbon tetrachloride, and ethylene dichloride azeotropically entrained with the carbon tetrachloride, travels up the column while liquid ethylene dichloride that is substantially free of chloroform and carbon tetrachloride is withdrawn from the reboiler via line 21. The ethylene dichloride withdrawn from the reboiler still contains impurities, chief among which are 1,1,2-trichloroethane and trichloroethylene, which may be removed by further processing with which this invention is not concerned.

The vaporous mixture from the reboiler rises through the rectifying section 11 of column 10 and is conveyed via line 22 to condenser 23 where the vaporous mixture is completely or partially condensed, the condensate being collected in accumulator 25. The condensate or reflux liquid is conveyed from accumulator 25 via line 26, pump means 27, and line 28 where it is introduced back into the top of column 10 at a point above the topmost rectifier plate. The reflux liquid flows down through the column, contacts the upflowing vapor stream from the reboiler, collects in the pool 17 from where it is conveyed to the reboiler thus beginning the cycle anew.

Overhead distillate is discharged from accumulator 25 via line 29, however, no overhead distillate is discharged until the concentration of chloroform in the reflux liquid exceeds 51.5 mole percent, at which point the carbon tetrachloride-ethylene dichloride azeotrope is broken, thus permitting recovery of ethylene dichloride that would otherwise be lost in the overhead distillate stream due to azeotropic entrainment. After the chloroform concentration of the reflux liquid reaches a level greater than 51.5 mole percent, overhead distillate may be continuously discharged provided the chloroform concentration is maintained at a level greater than 51.5 mole percent by continuous reflux as described herein.

It is, of course, to be realized that chloroform may be added to the system in order to effect a more rapid build up of the chloroform concentration or to maintain the chloroform concentration at the requisite level. For example, chloroform may be recovered from the overhead distillate discharged from the system and recycled to the column with the condensate or reflux liquid.

FIG. 2 graphically illustrates the effect of chloroform concentration on the relative volatility of a mixture of carbon tetrachloride and ethylene dichloride. At zero chloroform concentration, the relative volatility varies between 2.02 for 100 mole percent ethylene dichloride and 0.585 for 100 mole percent carbon tetrachloride, with a relative volatility of 1 at the azeotrope composition of 68 mole percent carbon tetrachloride and 32 mole percent ethylene dichloride.

It is seen from FIG. 2 that as the chloroform concentration increases, the carbon tetrachloride/ethylene dichloride ratio in the binary azeotrope also increases, and when the chloroform concentration exceeds 51.5 mole percent the relative volatility of the carbon tetrachloride-ethylene dichloride mixture becomes greater than 1. In other words, the azeotrope is broken.

The invention thus provides a straightforward, expedient means of separating carbon tetrachloride and chloroform impurities from crude ethylene dichloride which is further illustrated by the following examples.

EXAMPLE 1

The distillation unit used was a standard 1-inch diameter Oldershaw column provided with an overhead condenser and a reboiler consisting of a 1-liter round bottom flask which was heated by means of an oil bath. The feed to the column was pre-heated by pumping it through a glass coil immersed in an oil bath. The column contained 25 stripping plates and 31 rectifying plates.

A feed mixture of the type typically obtained upon catalytic oxyhydrochlorination of ethylene was continuously fed to the column at a rate of about 10 milliliters per minute.

The column was operated at atmospheric pressure at a reflux ratio (L/D) between 319 to 340, a distillate temperature between 65° C. to 71° C. and a reboiler pressure of 37.5 centimeters of water. The column was operated with continuous feed and discharge from the reboiler for about 11 hours with continuous reflux with no removal of overhead or light fraction, after which time a material balance run was begun and continued for 6.5 hours with continuous feed to the column, continuous discharge from the reboiler, continuous reflux, and continuous removal of overhead fraction.

The material balance for the feed, overhead, and reboiler is summarized as follows. All values are percent by weight.

| Constituents | Feed | Overhead | Reboiler |
| --- | --- | --- | --- |
| Ethylene Dichloride | 97.02 | 1.28 | 98.48 |
| Chloroform | 1.28 | 90.06 | 0 |

-continued

| Constituents | Feed | Overhead | Reboiler |
| --- | --- | --- | --- |
| Carbon Tetrachloride | 0.20 | 8.26 | 0 |
| Trichloroethylene | 0.19 | 0.02 | 0.17 |
| 1,1,2-Trichloroethane | 1.31 | 0 | 1.36 |
| Vinyl chloride | 0.02 | 0.04 | 0 |
| Vinylidene Chloride | — | 0.02 | 0 |
| 1,2-Dichloroethylene | — | 0.30 | 0 |
| Ethyl Chloride | — | 0.01 | 0 |

EXAMPLE 2

The procedure of Example 1 was followed except that the column was operated for only 3.5 hours with continuous feed and discharge from the reboiler and continuous reflux with no removal of light fraction prior to commencement of the material balance run. The overhead fraction contained 25.2 weight percent ethylene dichloride as compared with the overhead fraction of Example 1 which contained only 1.28 weight percent ethylene dichloride in which Example 1 the light fraction had been permitted to accumulate for a sufficient time in order to build up the chloroform content therein to break the carbon tetrachloride-ethylene dichloride azeotrope permitting substantial recovery of ethylene dichloride.

Although the invention has been described with specific references and specific details of embodiments thereof, it is to be understood that it is not intended to be so limited since changes and alterations therein may be made by those skilled in the art which are within the full intended scope of this invention as defined by the appended claims.

I claim:

1. In a process for purifying liquid ethylene dichloride by distillation wherein the impurities comprising carbon tetrachloride and chloroform are separated from the ethylene dichloride as a light fraction, the improvement comprising refluxing the light fraction until the chloroform concentration in the reflux exceeds 51.5 mole percent, thereafter maintaining the chloroform concentration in the reflux at greater than 51.5 mole percent and recovering ethylene dichloride that is substantially free of chloroform and carbon tetrachloride.

2. The improvement of claim 1 comprising adding chloroform to the system in order to effect a more rapid build up of chloroform concentration in the reflux or to maintain the chloroform concentration in the reflux at greater than 51.5 mole percent.

3. A process of separating ethylene dichloride from a liquid azeotropic mixture comprising ethylene dichloride and carbon tetrachloride comprising adding chloroform to the liquid azeotropic mixture so that the chloroform content of the resulting mixture is greater than 51.5 mole percent and distilling the resulting mixture to separate chloroform and carbon tetrachloride from the ethylene dichloride.

* * * * *